United States Patent [19]

Kaieda et al.

[11] Patent Number: 5,789,582

[45] Date of Patent: Aug. 4, 1998

[54] METHOD FOR PRODUCTION OF NUCLEAR HALOGENATED AROMATIC COMPOUND POSSESING CYANO GROUPS

[75] Inventors: Osamu Kaieda, Ibaraki; Koichi Hirota; Teruhisa Kajiwara, both of Hyogo; Norimasa Okuda, Ibaraki; Hisakazu Shindo, Hyogo; Yoshiro Hanayama, Hyogo; Yujin Shoda, Hyogo; Toyohiko Kohno, deceased, late of Hyogo, by Yasue Kohno, legal representative; Takashi Yodoshi, Ibaraki; Masaru Awashima, Osaka, all of Japan

[73] Assignee: Nippon Shokubai Co., Ltd., Osaka, Japan

[21] Appl. No.: 813,550

[22] Filed: Mar. 7, 1997

[51] Int. Cl.$^6$ .................. C09B 47/04; C07D 251/00; C07C 255/00

[52] U.S. Cl. .................. 540/122; 540/122; 544/180; 558/420; 558/425

[58] Field of Search .................. 540/122; 544/180; 558/420, 425

[56] References Cited

U.S. PATENT DOCUMENTS 5,565,612  10/1996  Pfirmann et al. .................. 558/425

Primary Examiner—Johann Richter
Assistant Examiner—Joseph Murray
Attorney, Agent, or Firm—Fish & Richardson P.C.

[57] ABSTRACT

A nuclear halogenated aromatic compound possessing cyano groups is produced by a method using as a raw material an aromatic compound which possesses cyano groups and assumes a solid state at room temperature and subjecting the raw material to a procedure comprising a step of melting and transporting the compound by a means transport-melting, a step of vaporizing the compound, a step of mixing the compound with a halogen gas, and a step of causing the vapor of the compound to react with the halogen gas in vapor phase in the presence of a catalyst sequentially in the order mentioned, which comprises maintaining a content of a self-condensate of the aromatic compound possessing cyano groups which arise during the melting of the aromatic compound possessing cyano groups in a gas of the compound which reacts with the halogen gas to a level of not more than 2.5 mol % based on the compound. The catalyst used in the method is activated carbon such that the average pore radius thereof determined by the nitrogen adsorption method is not less than 12.2 Å and the cumulative pore volume of the portion of the activated carbon having pore radiuses in the range of 5–100 Å determined by the steam adsorption method is not less than 0.45 g/cc.

16 Claims, 3 Drawing Sheets

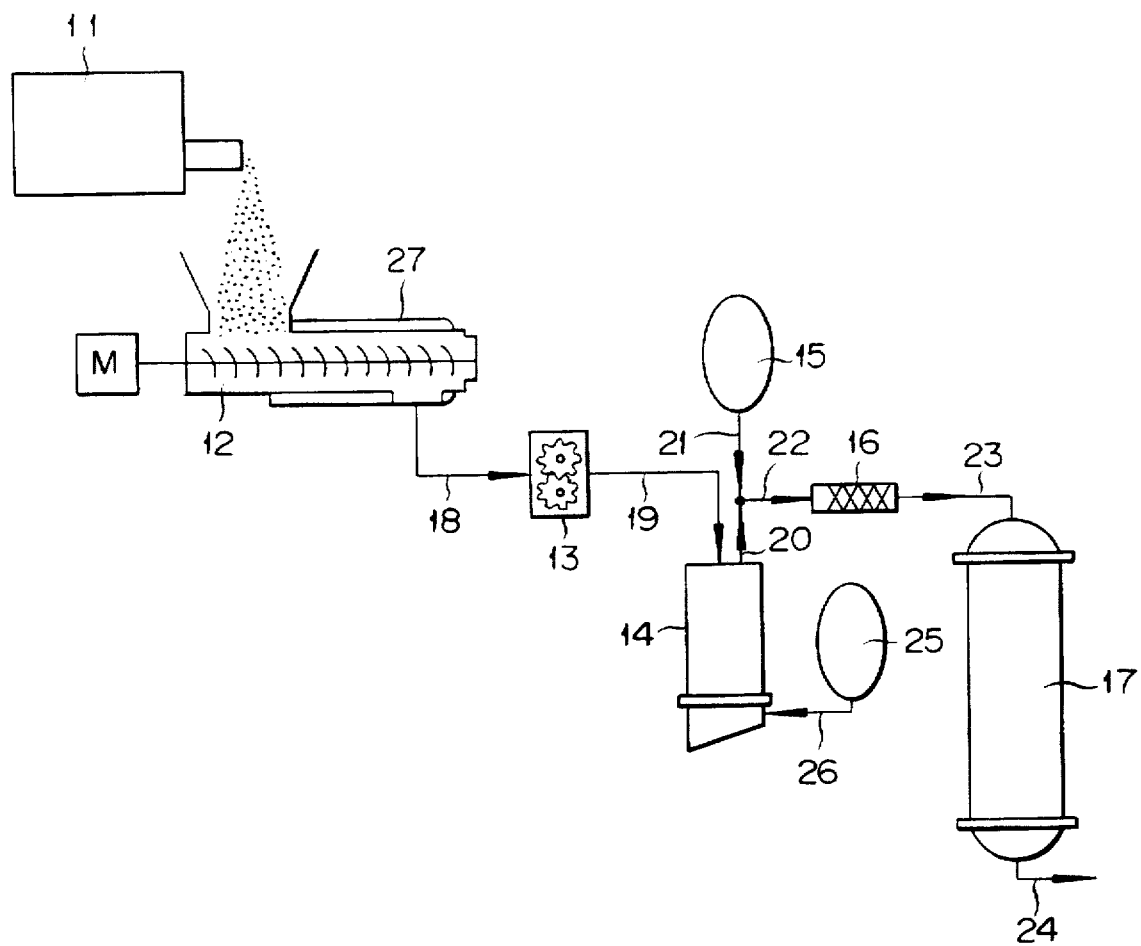

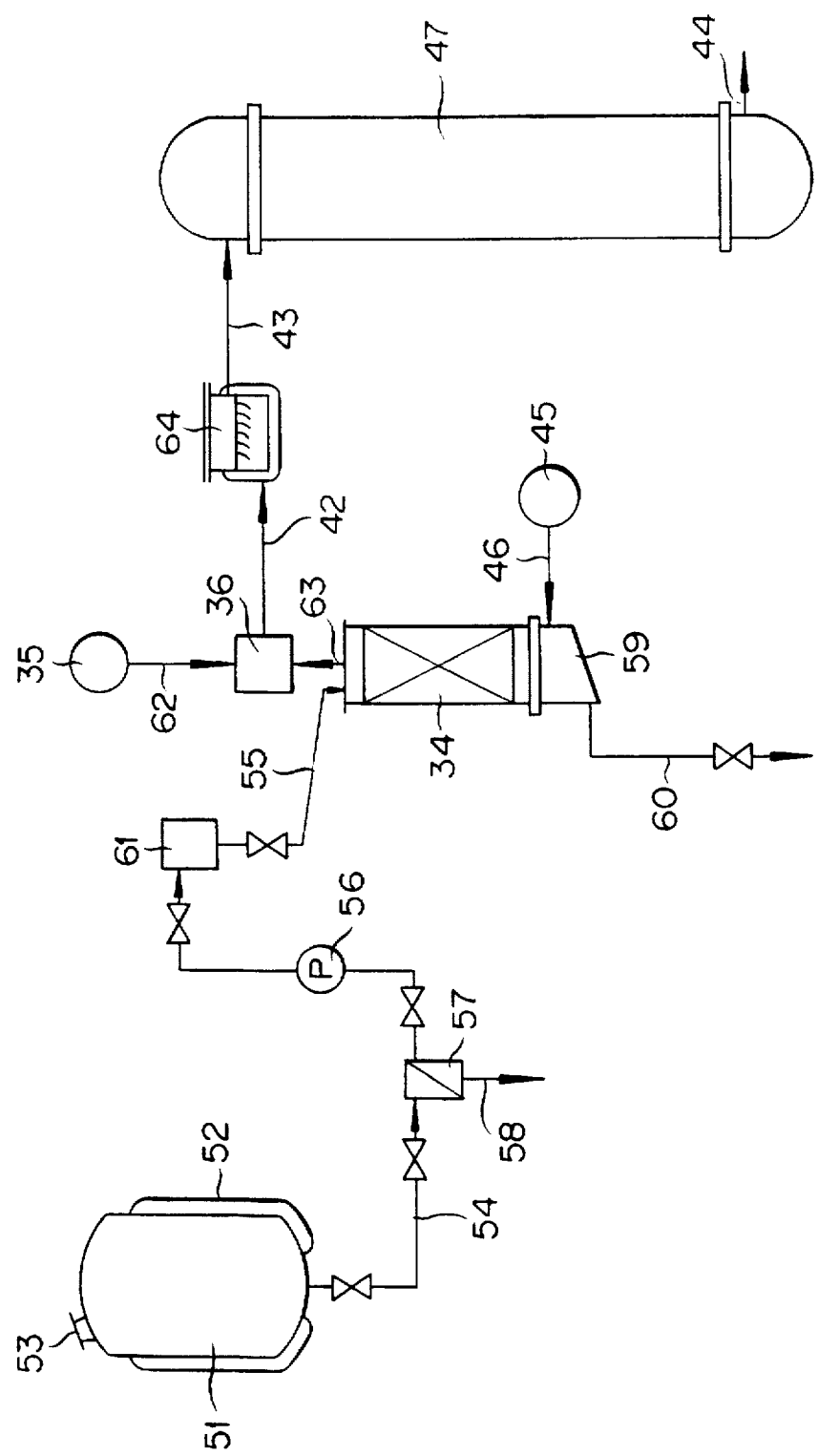

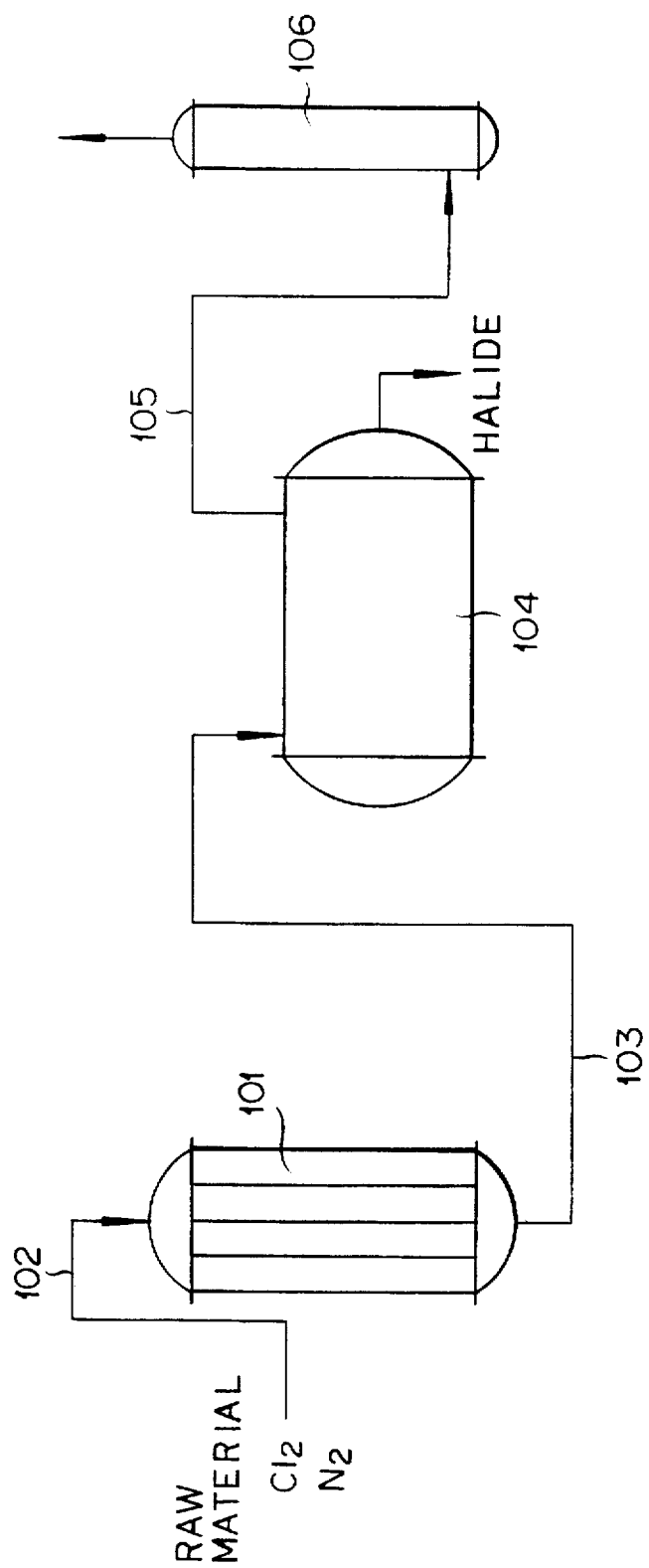

METHOD FOR PRODUCTION OF NUCLEAR HALOGENATED AROMATIC COMPOUND POSSESING CYANO GROUPS

BACKGROUND OF THE INVENTION

1. Field of the Invention

This invention relates to a method for producing a nuclear halogenated aromatic compound possessing cyano groups by causing a gas containing an aromatic compound possessing cyano groups to react with a halogen gas in the gaseous phase.

2. Description of the Prior Art

As methods for the production of nuclear halogenated aromatic compounds possessing cyano groups, methods for the production of tetrachloroorthophthalonitrile, for example, have been already known.

Saito et al., for example, disclose a method for producing tetrachlorophthalonitrile by the reaction of orthophthalonitrile with chlorine gas in gas phase in the presence of activated carbon as a catalyst in "Journal of Organic Synthetic Chemistry Society", Vol. 22, page 834 (1964). This report, however, fails to clarify the problems which arise in the commercialization of the method and, therefore, does not offer any definite measure for the solution of these problems. JP-B-50-38,089 and JP-B-63-65,065 also disclose similar methods. The methods which are disclosed specifically therein, however, are those for the production of tetrachloroisophthalonitrile. Similarly to the report regarding tetrachloroorthophthalonitrile, these patent publications do not clarify the problems which arise in the commercialization of the methods. Thus, no specific measure has been proposed for the solution of those problems which arise in the commercialization of nuclear halogenated aromatic compounds possessing a nitrile group..

Concerning the method for producing a nuclear chlorinated aromatic compound by the reaction of a gas containing an aromatic compound possessing cyano groups with chlorine gas in the gaseous phase, it is reported in "Journal of Organic Synthetic Chemistry Society," Vol. 22, pages 743–748 and ibid, pages 834–837 that activated carbon functions as an excellent catalyst possessing the activity of forming tetrachlorophthalonitrile in gas-phase catalytic chlorination of phthalonitrile. JP-B-44-29,853 has a mention to the effect that in the gaseous-phase catalytic chlorination of benzonitrile, activated carbon, for example, is capable of augmenting the production velocity of pentachlorobenzonitrile, also lowering the reaction temperature, and fulfilling an important role in precluding the decomposition of the nitrile group by chlorination which is liable to occur at elevated temperatures. The technical literature and the patent publications mentioned above have absolutely no description of the improvement of the service life of activated carbon as a catalyst and have not taken up this matter as a subject for study. Barely, "Journal of Organic Synthetic Chemistry Society" carries in Vol. 22, pages 834–837 thereof a report to the effect that the activity of activated carbon manifested in catalyzing the formation of tetrachlorophthalonitrile shows no sign of decline even after about 110 hours' use.

As respects the improvement of the service life of activated carbon as a catalyst, we have already published in "Journal of Organic Synthetic Chemistry Society," Vol. 47, pages 20–26, a report to the effect that activated carbon, as the optimum catalyst for the reaction of chlorination of benzonitrile, manifests the highest activity and high selectivity and that the service life of the catalyst can be expected to be elongated in proportion as the pore volume of the catalyst is increased.

Our knowledge as of the time of this publication, however, is based on the results regarding such pore volumes as embrace even a region of very large pore radiuses on the theory that the requirement necessary for the elongation of the service life of activated carbon as a catalyst resides solely in the parameter regarding pore volume. It, therefore, lacks perfect repeatability and even incurs the possibility that the long service life normally expected will not be obtained when the kind of catalyst is changed. Further, the largest pore volume, 0.95 cc/g, that is possessed at all by any of the activated carbon reported therein is equal to that of the activated carbon used as a catalyst in Control 1 which will be especially described herein below and the cumulative pore volume of the region of activated carbon possessing pore radiuses of 5–100 Å as determined by the steam adsorption method is only equivalent to 0.43 cc/g. Even when the activated carbon possessing the same pore volume of 0.95 cc/g as reported herein is adopted as a catalyst, therefore, the service life offered by this activated carbon never deserves to be called fully satisfactory. The desirability of further improving the activated carbon excelling in repeatability and enjoying a long service life as a catalyst has been finding widespread recognition for the sake of promoting commercialization. It may well be regarded as a task to be attained.

An object of this invention, therefore, is to provide a method for the production of a nuclear halogenated aromatic compound possessing cyano groups.

Another object of this invention is to provide a measure for the solution of the problems which arise in the production of a nuclear halogenated aromatic compound possessing cyano groups on a commercial scale.

The production of a nuclear halogenated aromatic compound possessing cyano groups by the reaction of a gas containing an aromatic compound possessing cyano groups with halogen gas in gas phase in the presence of a catalyst necessitates vaporization of a corresponding solid aromatic compound possessing cyano groups. The aromatic compound, before and after the vaporization, gives rise to various self-condensates of the aromatic compound possessing cyano groups. It has been found that these self-condensates entrain various problems such as clogging pipes, adhering to the catalyst so fast as to induce coalescence of catalyst particles and degradation of catalytic activity, or impairing the quality of the product. Still another object of this invention, therefore, is to provide a measure for the solution of these problems.

Yet another object of this invention is to provide, in the gas-phase catalytic halogenation of an aromatic compound possessing cyano groups, a method for the production of a nuclear halogenated aromatic compound possessing cyano groups by the use of activated carbon capable of retaining the activity to form the compound for a long time (long service life) and deserving high esteem as an excellent catalyst.

SUMMARY OF THE INVENTION

The objects described above are accomplished by a method for producing a nuclear halogenated aromatic compound possessing cyano groups by using as a raw material an aromatic compound which possesses cyano groups and assumes a solid state at room temperature and subjecting the raw material to a procedure comprising a step of melting and transporting the compound by a means for transport-melting, a step of vaporizing the compound, a step of mixing the compound with a halogen gas, and a step of causing the vapor of the compound to react with the halogen gas in a gas phase in the presence of a catalyst sequentially in the order mentioned, which comprises maintaining a content of a self-condensate of the aromatic compound possessing cyano groups in a gas of the compound which reacts with the halogen gas to a level of not more than 2.5 mol % based on the compound.

The objects are further accomplished by a method for producing a nuclear halogenated aromatic compound by causing the vapor of an aromatic compound possessing cyano groups to react with a halogen gas in a gas phase in the presence of a catalyst, which comprises using activated carbon as the catalyst and the activated carbon being such that the average pore diameter of the activated carbon determined by the nitrogen adsorption method is not less than 12.2 Å and the cumulative pore volume of the portion of the activated carbon having pore diameters in the range of 5–100 Å determined by the steam adsorption method is not less than 0.45 g/cc.

BRIEF DESCRIPTION OF THE DRAWINGS

FIG. 1 is a schematic process diagram illustrating one embodiment of the method for producing a nuclear halogenated aromatic compound possessing cyano groups according to this invention.

FIG. 2 is a schematic process diagram illustrating another embodiment of this invention.

FIG. 3 is a schematic process diagram illustrating yet another embodiment of this invention.

DESCRIPTION OF THE PREFERRED EMBODIMENT

The method according to this invention produces a nuclear halogenated aromatic compound possessing cyano groups by using as a raw material an aromatic compound which possesses cyano groups and assumes a solid state at room temperature (hereinafter referred to as "aromatic compound") and subjecting the raw material to a procedure comprising a step of melting and transporting the compound by a means for transport-melting, a step of vaporizing the compound, a step of mixing the compound with a halogen gas, and a step of causing the vapor of the compound to react with the halogen gas in gas phase in the presence of a catalyst sequentially in the order mentioned, which comprises maintaining a content of a self-condensate of the aromatic compound possessing cyano groups in a gas of the compound which reacts with the halogen gas to a level of not more than 2.5 mol %, preferably not more than 1.0 mol % based on the compound.

This invention also concerns a method for producing a nuclear halogenated aromatic compound by using as a raw material an aromatic compound which assumes a solid state at room temperature and subjecting the raw material to a procedure comprising a step of melting and transporting the aromatic compound (hereinafter referred to briefly as "melting-transporting step"), a step of vaporizing the compound (hereinafter referred to briefly as "vaporizing step"), and a step of mixing the vaporized compound with a halogen gas (hereinafter referred to briefly as "mixing step") sequentially in the order mentioned, and subsequently inducing a vapor phase catalytic reaction, which method is characterized in that the residence time in the molten state of the aromatic compound at the melting transporting step is not more than 120 minutes. The reason for imposing this upper limit on the residence time is that the ratio of formation of the self-condensates of the aromatic compound is liable to increase gradually in proportion as the residence time in the molten state of the aromatic compound at the melting transporting step is increased and that the clogging of pipes, the degradation of the catalytic activity, and the impairment of the product are actually induced particularly when the retention time exceeds 120 minutes.

Properly, therefore, the residence time in the molten state of the aromatic compound at the melting transporting step is shortened to the fullest possible extent. It is advantageous to set the preferable upper limit of the residence time at 60 minutes, and more preferable limit at 30 minutes.

The residence time mentioned above includes the time in which the solid aromatic compound begins to melt and partially solid compound exists as a slurry state in the melting compound.

The second means comprises setting the water content in the system for feeding orthophthalonitrile at a level below 2000 ppm, preferably below 1200 ppm, more preferably below 500 ppm, based on the amount of orthophthalonitrile. It has been found that the water contained mainly in the orthophthalonitrile as the raw material and also in the inert gas, the chlorine gas, and the ambience participates in the condensations together with the molten orthophthalonitrile and the vaporized orthophthalonitrile and consequently (A) heighten the ratio of formation of the phthalocyanine compounds which are mainly formed during the vaporization of orthophthalonitrile and (B) heightens the ratio of formation of chain polymolecular compounds of orthophthalonitrile represented by the (a) general formula (1) which are mainly formed during the vaporization of orthophthalonitrile (specifically, chain dimers of orthophthalonitrile, chain trimers of orthophthalonitrile, chain tetramers of orthophthalonitrile, chain pentamers of orthophthalonitrile, chain hexamers of orthophthalonitrile, chain heptamers of orthophthalonitrile, and chain octamers of orthophthalonitrile), particularly chain trimers of orthophthalonitrile and (b) cyclic polymolecular compounds of orthophthalonitrile among others cited above which are predominantly formed, and especially 2,4,6-tri(o-cyanophenyl)-1,3,5-triazine which is formed copiously.

The formation of the self-condensate, therefore, can be very easily repressed by controlling the water content in the raw materials to be used (orthophthalonitrile, inert gas, and chlorine gas) and designing the feed system in a closed construction capable of preventing the entry of water from the ambience. When the water content is large, orthophthalonitrile is hydrolyzed to give rise to such organic acids as orthophthalic acid. The organic acids thus formed give birth to metal salts. Generally, the organic acids thus formed participate in the formation of self-condensate. Thus, the repression of the formation of organic acids is advantageous for this invention.

The produced amount of the self-condensate can be suppressed to not more than 2.5 mol %, preferably not more than 1.0 mol % to the aromatic compound possessing cyano groups by appropriate combination of control of such residence time and control of water content or by controlling such individual conditions.

Then, in the method of this invention for the production of the halogenated aromatic compound, the measure to solve the problems (one requirement for construction) by limiting the residence time in the molten state of the aromatic compound at the melting-transporting step, a major component of the method, can be carried out by an implement (device) illustrated in FIG. 2, namely by a procedure which comprises feeding the aromatic compound as the raw material in a solid state through a feed inlet 53 into a melting device 51 provided with a heating jacket 52, heating and melting the raw material therein at a temperature exceeding the melting point thereof and then feeding the molten aromatic compound via pipes 54 and 55 and a transfer pump 56 to an evaporator 34 of the next step.

As the melting means for fulfilling the role of melting the solid raw material which is equivalent to the former half part of the role of the means disclosed above, any of the known devices and mechanisms such as, for example, the melting devices provided with a heating and a stirring mechanism, i.e. those represented by the aforementioned melting device provided with a heating jacket, may be suitably utilized. For the heating mechanism, a jacket type member adapted to enclose the device with a jacket and heat the device by means of a heat medium circulated through the jacket or a heater type member adapted to encircle the device with a heater and heating the device by energizing the heater may be used. For the stirring mechanism, a motor drive type member adapted to combine paddle vanes or turbines fit for stirring a solid-liquid system with such a drive device as a motor may be used. In the melting device mentioned above, the mechanism can be completed by being fixed to a closed device (melting device) which has undergone a treatment for imparting resistance to heat and to chemicals enough to deal with raw materials in a volume fit for commercialization and which is provided with an inlet and an outlet.

The molten raw material in the melting device may also be transported to the evaporation step by controlling a head pressure.

As the liquid transport means for fulfilling the role of transporting the raw material in a molten state which is equivalent to the latter half part of the role of the means disclosed above, the former and latter devices (melting device 51 and evaporator 34) can be interconnected with the pipe 55 and the transfer pump 56, a kind of liquid transport device, can be operated to transfer the solution through the pipes. As typical examples of the liquid transport device, centrifugal pumps such as volute pump, turbine pump, rubber-lined sand pump, chemical pump, slurry pump, vertical pump, and propeller pump, reciprocating pumps such as direct-acting pump, plunger pump, Milton Roy pump, and diaphragm pump, and rotary pumps such as gear pump, partition pump, screw pump, and Wesco pump may be cited. Any of these known pumps may be suitably utilized as the liquid transport means mentioned above.

When the disclosed means (device) mentioned above is given a scale-up necessary for commercialization, it is destined to retain in a molten state the solid aromatic compound placed as the raw material in an amount fit for commercialization in the melting column. This part of the device constitutes itself a velocity controlling step such that the residence time of the raw material in the molten state therein may be lowered below 120 minutes. The preferred decrease of the residence time to below 60 minutes or even below 30 minutes is attained only with difficulty because it entails an addition to the relevant devices and facilities.

As a solution for the problem mentioned above, the present inventors have found a process which is characterized by using the raw material feed means for feeding the solid raw material to the transporting-melting means at the melting-transporting step, using the transporting-melting means for melting the solid raw material in the course of transportation, and further optionally using liquid feed means for feeding the molten raw material to the subsequent vaporizing step. This process allows the residence time to be lowered to below 60 minutes, or even below 30 minutes as preferred for the purpose of commercialization. Now, this process will be described in detail below with reference to drawings. FIG. 1 is a schematic process diagram illustrating one preferred embodiment of the method of this invention for the production of the nuclear halogenated aromatic compound.

The method of this invention for the production of the nuclear halogenated aromatic compound, as illustrated in FIG. 1, accomplishes this production by using as a raw material an aromatic compound assuming a solid state at room temperature, subjecting this raw material to a procedure which comprises a melting-transporting step, a vaporizing step, and a mixing step, and performing a vapor-phase catalytic reaction on the resultant mixture, which method is characterized by using raw material feed means 11 for feeding the raw material in the solid state to transporting-melting means 12 at the aforementioned melting-transporting step, then using the transporting-melting means 12 for melting the solid raw material during the course of transportation, and subsequently using liquid feed means 13 capable of interconnecting the transporting-melting means 12 and the evaporator 14 with pipes 18 and 19 and transporting a liquid through the pipes for feeding the raw material now in a molten state to the evaporator 14 of the subsequent vaporizing step.

The raw material feed means 11 has no particular limit to impose and can be suitably selected from all the known means because the raw material to be handled thereby assumes a solid state at room temperature and, therefore, obviates the necessity for paying due respect to the factor of residence time which ties a molten substance. To be more specific, it is a device for transporting a raw material in a solid state from a raw material storage column such as, for example, a hopper or a raw material storage part within a device over a short distance to the transporting-melting means 12. A standard feed device which is capable of transporting a raw material in a specific amount over a short distance, for example, can be utilized.

The feed devices which are utilizable for the raw material feed means 11, therefore, can be broadly divided into those of the dropping type which rely solely on gravitational attraction to effect the movement of the raw material and those of the horizontal type which use mechanical force for moving the raw material. The gravitational feed devices of the dropping type include chute feed devices of the gate (sluice valve) type and the damper (stop valve) type, rotary feeders (horizontal axis), and table feeders, for example. The mechanical force feed devices of the horizontal type include endless feed devices of the movable container type such as (continuous) belt feeders and (split) bucket (pan) feeders and the stationary container type such as (open) drag (flight) conveyors and (closed) float conveyors, thrust feed devices of the reciprocating type such as vibration feeders and shaking feeders and the screw type such as screw feeders, and pneumatic feed devices of the high air pressure such as injection (ejector) feeders and the low air pressure such as air slides, for example. Preferably, the various feed devices mentioned above are provided with a metering feed mechanism. The provision of the metering feed mechanism is preferred because it allows the raw material to be continuously fed in a fixed amount to the transporting-melting means 12 and facilitates the control of such factors as the residence time of the raw material in the molten state.

Though the device which is provided with the metering feed mechanism mentioned above does not need to be particularly limited, the screw type metering feeder is preferably used because it possesses a simple construction, allows the continuous metered supply of a given material to be easily adjusted and controlled, and suffers only sparingly the entry of the moisture from the ambient air owing to the tightly sealed construction. As typical examples of the screw type feeder which can be used herein, spiral feeders produced by Seishin Kigyo K.K., screw feeders produced by Taisei Kogyo K.K., accurate feeders produced by Nippon Pneumatic Kogyo K.K., KRC kneaders produced by Kurimoto Tekkosho K.K., and twin-screw feeders produced by K-Tron K.K. may be cited.

Next, the transporting-melting means 12 has no particular limit to impose but is only required to be capable of melting the solid raw material during the course of transportation so as to allow the molten material a residence time of not more than 60 minutes, or even not more than 30 minutes. Any of the known means that answer this description can be suitably utilized. To fulfill this requirement, a standard transporting device which is provided with a heating mechanism can be used. Preferably, a continuous (synonymous with the operation of a metering feed mechanism) mixing-transforming device which is so provided with a heating mechanism as to conform with the change of the state of aggregation of a given raw material from the solid state through a viscous state offering high resistance to deformation to the molten state is utilized.

As typical examples of the continuous mixing-transporting device mentioned above, continuous mixing-transporting devices of the twin-axis screw type, multiple-axis paddle (pug mill) type, high-speed rotary disc type, self-cleaning type, uni-axial rod type, votator type, marler type, mill type, cokneader type, twin-axis screw extrusion type, and tapered roll type and continuous mixing-transporting devices of the type suitably combining the devices mentioned above may be cited. Among other devices cited above, the twin-axis kneader type continuous mixing-transporting devices having the twin-screw type and the twin axis paddle type combined as arranged after the fashion of the self cleaning type prove particularly advantageous. In the twin-axis kneader type continuous mixing-transporting device mentioned above, paddles and screws are incorporated in suitable numbers around two horizontally parallel shafts and the paddles paired laterally are always set as biassed with a phase of 90° and are rotated at one same speed in one same direction. In each pair of paddle and screw, since the two members so rotate that the leading end of either of them always rubs the other, the raw material, be it even so viscous, produces a fully satisfactory self-cleaning action. Further, by decreasing the clearance between a trough and the paddle, the adhesion of the raw material to the paddle, screw, and trough can be repressed to a point where the self-cleaning action will be enhanced. Since the raw material, therefore, can be transported without any waste, the residence time of the raw material in the device can be reduced. This device has a further advantage that the residence time can be adjusted by suitable recombination of paddles and other components. As the twin axis kneader type transporting device, the KRC kneader produced by K.K. Kurimoto Tekkosho may be used.

As the heating mechanism for the aforementioned continuous mixing-transporting device provided with a heating mechanism, a jacket type member 27 which, as illustrated in FIG. 1, is adapted to enclose the device with a jacket and heat the device by means of a heat medium circulated through the jacket or a heater type member adapted to encircle the device with a heater and heating the device by energizing the heater may be used. When the temperature imparted by the heating mechanism is unduly high relative to the melting point of the aromatic compound as the raw material, the aromatic compound will be transformed into a polymolecular compound. Generally, therefore, it is set in a range from the melting point of the aromatic compound as the raw material to 80° C. higher than the melting point, preferably in a range of 5°–50° C. higher than the melting point of the aromatic compound. So long as the heating mechanism has the highest operating temperature thereof set in the neighborhood of 250° C., therefore, it can handle an aromatic compound having a relatively high melting point fully satisfactorily.

The liquid feed means 13 mentioned above has no particular limit to impose but is only required to feed the molten aromatic compound to the subsequent vaporizing step. Any of the known means that answer the description can be suitably utilized. To fulfill the requirement, a standard hot liquid transferring device formed by interconnecting the transporting-melting means 12 and the evaporator 14 with the pipes 18 and 19 and operated by transporting the raw material through the pipes can be used, for example.

As typical examples of the hot liquid transporting device which can be used herein, centrifugal pumps such as diaphragm pump, volute pump, turbine pump, rubber-lined sand pump, chemical pump, slurry pump, vertical pump, and propeller pump, reciprocating pumps such as direct-acting pump, plunger pump, Milton Roy pump, and diaphragm pump, and rotary pumps such as toothed-wheel (gear) pump, partition (vane) pump, thread (screw) pump, and Wesco pump may be cited. Preferably, the hot liquid transferring device is provided with a metering feed mechanism. It is properly provided with a metering feed mechanism which is capable of stably feeding the raw material in a fixed amount in spite of the vapor pressure (back pressure) generated within the evaporator 14 which is connected with pipes. The aforementioned hot liquid transporting device provided with the metering feed mechanism effects the transportation of the liquid, for example, by disposing inside a casing a toothed wheel, a partition, or screw adapted to produce virtually no clearance relative to the casing, setting the toothed wheel or the like rotating, and causing the liquid to be entrapped in the gap and propelled. Where the flow of the liquid must be uniform (so as to suit the operation of metering) and require high pressure (back pressure), a rotary pump such as a gear pump, a vane pump, a screw pump, or Wesco pump which fits the transportation of a raw material of high viscosity can be used. This invention allows a check valve or a back pressure valve to be interposed between the liquid feed means 13 and the evaporator 14 so as not to be affected by the inner pressure generated in the evaporator, the reaction vessel, and the collector vessel. This invention also permits a cushion tank to intervene between the transporting-melting means 12 and the liquid feeding means 13. This provision of the cushion tank further stabilizes the metering transportation.

The liquid feed means 13 mentioned above is an optional component for the construction. The raw material molten by the transporting-melting means 12, when occasion permits, may be fed directly to the evaporator 14 through no medium of the liquid feed means 13. Particularly when such a device as the continuous mixing-transporting device provided with a heating mechanism which is vested with a metering feed function is utilized as the transporting-melting means 12, this device additionally fulfills the requirement imposed on the liquid feed means 13 mentioned above and it allows the transportation of the molten raw material to the evaporator by placing the transporting-melting means 12 at a higher level than the evaporator 14 and adjusting the head consequently generated therebetween. In this case, therefore, the necessity for additionally providing the liquid feed means 13 is scant and the residence time can be shortened.

After the solid raw material has been heated and molten by the transporting-melting means 12, it not required to be heated any further but is required to be retained in the molten state until it is fed to the evaporator 14 at the subsequent step. The devices and the pipes which exist in the route for transporting the raw material between the point at which the solid raw material is molten by the transporting-melting means 12 and the point at which the molten raw material is supplied to the evaporator 14 are preferred to be provided with members capable of heating and cooling for retaining the raw material in a prescribed temperature range and/or members capable of keeping the raw material warm.

The mode of executing the melting-transporting step which constitutes itself the main component of the construction of this invention has been described. The portion of the method of production which follows the melting-transporting step has no particular limit to impose. Naturally, it can be carried out by suitably utilizing the known method for the production of an aromatic halide. The aforementioned portion of the method of production will be briefly described below with reference to proper means (mode of execution) illustrated in FIG. 1.

First, at the vaporizing step, as the device which is provided as, for example, with a heating mechanism intended as vaporizing means, the evaporator 14 is used for vaporizing the raw material transported from the melting-transporting step in a molten state.

The aforementioned evaporator 14, to be effectively used herein, may be so designed that the vaporization of the aromatic compound is effected by feeding the aromatic compound in a molten state to the evaporator 14 through the upper part thereof and feeding an inert gas thereto from an inert gas tank 25 via an inert gas pipe 26 as illustrated in FIG. 1. The material of the inner surface of the evaporator which is destined to contact the aromatic compound properly is a nonmetallic substance, preferably a glass lining, for the purpose of precluding the occurrence of a self-condensate. The temperature of the evaporator is only required to exceed the dew point of the aromatic compound to be used. Properly, it is in the range from the dew point of the aromatic compound to 120° C. higher than the dew point, preferably in the range of 20°–80° C. higher than the dew point of the aromatic compound. When the aromatic compound possessing cyano groups isorthophthalonitrile, it is preferably in the rage of 139°–300° C. As typical examples of the inert gas mentioned above, nitrogen gas, hydrogen chloride gas, and carbon tetrachloride gas may be cited. Particularly for this invention, it is advantageous to use nitrogen gas.

Then, at the mixing step, a gas-gas type line mixer 16 such as, for example, a static mixer adapted to be disposed somewhere in the whole length of pipes is used as mixing means for the sake of imparting continuity to the mixing operation. The vaporized aromatic compound fed from the aforementioned evaporator 14 through the interiors of pipes 20 and 22 and a halogen gas fed from a halogen gas tank 15 through the interiors of a pipe 21 and the pipe 22 are mixed in the line mixer 16 and the resultant mixed gas is fed to the reaction system through the interior of a pipe 23.

The mixed gas obtained through the steps mentioned above is fed to the upper part of a halogenating reaction vessel 17 packed with a catalyst through the pipe 23. It is caused to undergo a continuous vapor phase catalytic reaction while it is being passed through the interior of the reaction vessel 17 at a prescribed reaction temperature for a prescribed reaction time. Then, the gas formed by the reaction is discharged from the lower part of the halogenating reaction vessel 17 through a pipe 24 and the halogenation product is cooled to produce an aromatic halogenated compound in the form of a powder of crystals. The gaseous residue remaining after the formation of crystals, when necessary, may be washed with an alkali to remove the unaltered halogen or by-produced hydrogen halide.

The catalyst which is packed in the halogenating reaction vessel mentioned above may be any of all the catalysts that are effective in the vapor phase halogenation. It is particularly advantageous to use activated carbon or a composite having a metallic salt deposited on activated carbon. Though the reaction temperature is variable with the kind of aromatic compound to be used, the reaction is properly carried out at a temperature in the range of 220°–450° C. When tetrachlorophthalonitrile is produced, a temperature range of 250°–350° C. is preferable. Optically, the amount of the halogen gas is 1.2 to 2 times the theoretical amount. It is allowable to use the halogen gas in an amount more than several times the theoretical amount by increasing the space velocity and reclaiming the unaltered halogen gas for cyclic use. Though the reaction is generally carried out in the neighborhood of normal pressure, it may be performed under a decreased pressure or an increased pressure. The reaction can be carried out in a fixed bed or a fluidized bed, whichever better fits the occasion. Further in this invention, for the sake of commercializing the production of the nuclear halogenated aromatic compound, it is advantageous to automate completely all the process devices and facilities to enable all the steps of production of this invention to be operated stably and continuously by automatic control.

The method for the production of a nuclear halogenated aromatic compound according to this invention makes surpress formation of the self-condensate of the compound by controlling the residence time (controlling the water content appropriately if necessary) and choosing a method for controlling, but in the present invention it can also to carry out by removing the self-condensate from the aromatic compound, and thereafter causing the vapor of the aromatic compound and a halogen gas together with an inert diluting agent or in the absence of the inert diluting agent to undergo a vaporphase reaction in the presence of a catalyst.

That is, in accordance with the present invention, in the evaporation step for vaporizing the aromatic compound, a condensing portion is provided in the evaporator maintaining a temperature exceeding the dew point of the aromatic compound preferably in the range of the dew point of the aromatic compound to 120° C. higher than the dew point, more preferably in the range of 20°–80° C. higher than the dew point, the self-condensate of the aromatic compound possessing cyano groups is liquefied and then the self-condensate comprising these liquid materials is removed on demand from the condensing portion.

The self-condensate formed in the present invention is explained by orthophthalonitrile as an example of the aromatic compound possessing cyano groups.

FIG. 2 is a schematic process diagram illustrating a typical embodiment of a process for production of tetrachloroorthophthalonitrile as the nuclear halogenated aromatic compound possessing cyano groups, and an embodiment of the method for removing the above mentioned self-condensate referring the above mentioned diagram as follows:

First, the term "self-condensate of orthophthalonitrile" as used herein refers to the compounds represented by the general formula (1)

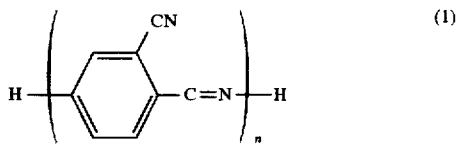

wherein n is an integer of 2–8. As typical examples of these compounds, the following compounds may be cited.

1. Chain polymeric compounds of orthophthalonitrile

The chain polymeric compounds of orthophthalonitrile include chain dimers of orthophthalonitrile, chain trimers of orthophthalonitrile, such as those of the general formula (2)

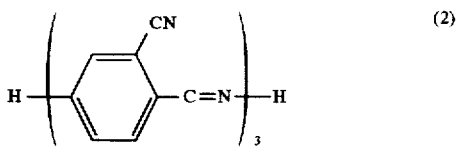

chain tetramers of orthophthalonitrile, chain pentamers of orthophthalonitrile, chain hexamers of orthophthalonitrile, chain heptamers of orthophthalonitrile, and chain octamers of orthophthalonitrile, for example.

Particularly, since chain trimers of orthophthalonitrile predominantly occur as chain polymeric compounds of orthophthalonitrile, this invention prefers to remove the chain trimers of orthophthalonitrile.

2. Phthalocyanine compounds

The phthalocyanine compounds include non-metal phthalo-cyanine, iron phthalocyanine, nickel phthalocyanine, chromium phthalocyanine, zinc phthalocyanine, copper phthalocyanine, manganese phthalocyanine, and cobalt phthalocyanine, for example.

3. Cyclic polymeric compounds of orthophthalonitrile

The cyclic polymeric compounds of orthophthalonitrile include 2,4,6-tri(o-cyanophenyl)-1,3,5-triazine, for example.

The method for removing the aromatic compound possessing cyano groups is explained by using orthophthalonitrile as an example of the aromatic compound.

In the present invention, the self-condensate of orthophthalonitrile is removed from the orthophthalonitrile vapor by liquefying it.

The orthophthalonitrile to be vaporized may be molten in advance or, when occasion demands, may be in a solid state at the time of the vaporization, as explained in the control of the residence time. When it is used in the molten state, the method which comprises melting the compound in advance in a melting device installed exclusively for the purpose of melting and feeding the molten compound in a required amount from the melting device or the method which comprises melting the compound in an amount conforming to the feeding speed and feeding the molten compound may be used, whichever better suits the occasion, by the melting means used in the controlling method for the residence time.

The evaporator which is required for the purpose of the vaporization in this invention may be of the type adapted to effect the vaporization of orthophthalonitrile by feeding orthophthalonitrile from above and feeding an inert gas such as, for example, nitrogen gas from below or of the type adapted to effect the vaporization of orthophthalonitrile by charging an evaporator with orthophthalonitrile in advance and thereafter feeding an inert gas such as, for example, nitrogen gas into a liquid obtained by melting. As the evaporator, a thin film evaporator may be used which is adapted to receive supply of orthophthalonitrile in a molten state and vaporize this molten orthophthalonitrile.

In the evaporator which is required for the vaporization in this invention, the inner surface thereof which is destined to contact orthophthalonitrile is properly formed of a non-metallic substance, preferably glass lining. The evaporator of the type which effects the vaporization of orthophthalonitrile by adding orthophthalonitrile in a preparatorily molten state from above and feeding such an inert gas as nitrogen gas from below may be utilized or the evaporator of the type which attains the vaporization of orthophthalonitrile by preparatorily placing orthophthalonitrile in a solid state in the evaporator, then melting this solid orthophthalonitrile, and feeding such an inert gas as nitrogen gas into the molten raw material may be used, whichever better suits the occasion.

Though the temperature of the evaporator is only required to be not lower than the dew point of orthophthalonitrile, it is preferably in the range of 139°–300° C., more preferably in the range of 150°–230° C. The evaporator, by being kept at this temperature, is enabled to liquefy the self-condensate of orthophthalonitrile during the vaporization of orthophthalonitrile. The liquefied self-condensate of orthophthalonitrile can be separated from orthophthalonitrile in a condensing part which is disposed in the interior, preferably in the lower part, of the evaporator. Properly, the separated self-condensate of orthophthalonitrile is extracted from the condensing part from time to time.

The self-condensate of orthophthalonitrile which can be liquefied at the same time that orthophthalonitrile is vaporized is mainly a chain polymeric compound, particularly a chain trimer, of orthophthalonitrile represented by the general formula (1) mentioned above. These chain polymeric compounds may contain phthalocyanine compounds which are other solid self-condensates of orthophthalonitrile or cyclic polymeric compounds of orthophthalonitrile in a slurry state.

According to the present invention, the self-condensate obtained can thus be removed. Further, in the present invention, the self-condensate can effectively removed by combining the following two methods on demand. In case of ortho-phthalonitrile, the compound is explained in detail.

The first method effects the removal of the self-condensate of orthophthalonitrile by separating the solid self-condensate of orthophthalonitrile which occurs while orthophthalonitrile is molten from the molten orthophthalonitrile.

That is, a filtering part is provided which is kept at a temperature exceeding the melting point of orthophthalonitrile either at the same time that orthophthalonitrile is molten or thereafter and this filtering part is used to separate the solid self-condensate of orthophthalonitrile generated during the melting of orthophthalonitrile. Then, the self-condensate of orthophthalonitrile separated by filtration is extracted from the filtering part from time to time.

The self-condensate of orthophthalonitrile which occurs while the orthophthalonitrile is molten is predominantly phthalocyanine compounds. These phthalocyanine compounds may contain cyclic polymeric compounds which are other self-condensates of orthophthalonitrile.

When the aromatic compound, melting device is used for melting, the inner surface of the evaporator fated to contact orthophthalonitrile is properly made of a nonmetallic substance, preferably glass lining. For example, the melting column may be constructed for a batchwise operation which comprises preparatorily placing orthophthalonitrile in a solid state in the melting device, then heating and melting the solid compound, and thereafter transferring the molten compound to the evaporator or for a continuous operation which comprises feeding orthophthalonitrile powder from time to time from above to the melting column kept in a heated state and melting the powdery compound therein, extracting the molten orthophthalonitrile from below the melting column, and continuously adding the molten orthophthalonitrile to the evaporator from above through a pipe having the inner surface thereof made of a non-metallic substance. Though the temperature of the melting column is only required to be not lower than the melting point and lower than the boiling point of orthophthalonitrile, it is appropriately in the range of 139°–300° C., preferably in the range of 150°–200° C.

The second method effects the removal of the self-condensate of orthophthalonitrile by either solidifying or liquefying the self-condensate of orthophthalonitrile which is contained in the orthophthalonitrile-containing gas resulting from the vaporization of orthophthalonitrile and separating the solid or liquid self-condensate from the orthophthalonitrile vapor, in case of ortho-phthalonitrile as the aromatic compound.

Specifically, a collecting part which is fabricated of a reticulate substance so as to allow collection of solid substance is placed in a stream of orthophthalonitrile-containing gas and is used to either solidify or liquefy the self-condensate of orthophthalonitrile. Then, from the collecting part, the solid or liquid self-condensate of orthophthalonitrile is extracted from time to time.

As typical examples of the reticulate substance, metal gauze, glass wool, porous plate, filter, honeycomb, and porous sheet may be cited.

This collecting part can collect the solid substance in the form of mist. The collecting device, by keeping the temperature thereof at the lowest possible level above the dew point of orthophthalonitrile, is enabled to condense a sublimable solid substance. Preferably, the collecting device is kept at a temperature in the range of 180°–250° C.

Preferably, the self-condensate of orthophthalonitrile which is collected by this collecting device is predominantly 2,4,6-tri)o-cyanophenyl)-1,4,5-triazine compound. The substance partly assumes the form of mist or a sublimed state, in the mixed vapor. The collecting device mentioned above is capable of effectively collecting the substance.

The collecting part is also capable of collecting the chain polymeric compounds of orthophthalonitrile which are other self-condensates of orthophthalonitrile. This collecting part can collect phthalocyanine compounds which are self-condensates of orthophthalonitrile.

The orthophthalonitrile vapor which remains after the removal of the self-condensate of orthophthalonitrile by such a method as mentioned above produces tetrachlorophthalonitrile when it reacts with chlorine gas in a vapor phase in the presence of a catalyst. In the orthophthalonitrile-containing gas which remains after the removal of the self-condensate of orthophthalonitrile in this case, the content of the self-condensate of orthophthalonitrile is preferred to be lowered below 2.5 mol %, particularly below 1.0 mol %, based on the amount of orthophthalonitrile. If the content of the self-condensate of orthophthalonitrile is unduly large, the disadvantage arises that the excess will deposit on the catalyst to induce coalescence of catalyst particles and degradation of the catalytic activity. Further, the extraction of the catalyst of degraded activity from the reaction vessel will not be easily obtained.

FIG. 2 is a process flow sheet schematically representing a typical mode of executing the method for the production of tetrachloroorthophthalonitrile as a nuclear halogenated aromatic compound possessing cyano groups according to this invention. Now, the mode of embodying the method for removing the self-condensate will be described below with reference to the flow sheet.

With reference to FIG. 2, in the method for the production of tetrachloroorthophthalonitrile according to this invention, orthophthalonitrile in a solid state such as, for example, in the form of powder is fed from time to time to a melting device 51 lined with glass and provided with heating means such as, for example, a heating jacket 11 and molten therein by being heated to a temperature exceeding the melting point thereof. Then, during the introduction of the molten orthophthalonitrile through a conduit 54 and a pump 56 to the evaporator 34, the molten orthophthalonitrile is passed through a filter such as, for example, a strainer 57 interposed between the melting device 51 and the evaporator 34 to separate the self-condensate (mainly a phthalocyanine compound) of orthophthalonitrile formed in a solid state in the melting device 51. The self-condensate is removed from time to time through a conduit 58 (operation of removal before vaporization).

Then, the molten orthophthalonitrile which has been passed through the strainer 57 is continuously fed, optionally via a receptacle 61 for a molten raw material, to the upper part of the evaporator 34 and an inert gas (such as, for example, nitrogen gas) from an inert gas tank 45 to the lower part of the evaporator 34 respectively through a conduit 55 and a conduit 46 to vaporize the mixture of the orthophthalonitrile and the inert gas at a temperature above the dew point of orthophthalonitrile. Simultaneously with this vaporization, the self-condensate (mainly a chain polymolecular compound of orthophthalonitrile) is condensed at a condenser 59 installed in the lower part of the evaporator 34 and extracted from time to time from the lower part of the condenser 59 through a conduit 60 (operation of removal during vaporization).

Then, the mixture of the orthophthalonitrile vapor with an inert gas and a halogen gas such as, for example, chlorine gas from a halogen gas tank 35 are continuously fed respectively via conduits 62 and 63 and mixed in the mixer 36. The resultant gaseous mixture is introduced via a conduit 42 into a collector such as, for example, a trap 64 interposed between the evaporator 34 and a reactor 49 and retained above the dew point of ortho-phthalonitrile for the purpose of collecting the self-condensate of orthophthalonitrile contained in the orthophthalonitrile vapor and the self-condensate (mainly cyclic polymolecular compound of orthophthalonitrile) of orthophthalonitrile contained in the orthophthalonitrile-containing gas is separated from the gaseous mixture until the content of the self-condensate falls below 2.5 mol %, preferably below 1.0 mol % based on the amount of ortho-phthalonitrile (removal after vaporization).

Subsequently, the gaseous mixture from which the self-condensate of orthophthalonitrile has been lowered to a prescribed content is introduced via a conduit 43 into a reactor 47 packed with a catalyst such as, for example, activated carbon and left reacting at a prescribed reaction temperature for a prescribed reaction time. The gas formed by this reaction and emanating from the reactor 47 is discharged via a conduit 44. Then, the product of halogenation is cooled to obtain tetrahaloorthophthalonitrile such as, for example, tetrachloroorthophthalonitrile in the form of a powder of crystals. The gaseous substance remaining after the formation of crystals may be washed with an alkali, when necessary, for the removal of the unaltered chlorine and the by-produced hydrogen chloride.

It is advantageous to repress the formation of the self-condensate of orthophthalonitrile in the feed system and vaporize orthophthalonitrile, further obtain the mixed gas of orthophthalonitrile vapor with chlorine gas, introduce this mixed gas into a reaction system, and induce the reaction thereof as described above.

In this invention, the orthophthalonitrile on the feed system side is required to assume a vaporized state by the time it ultimately reaches the reaction system. The means to effect this vaporization has no particular limit to impose. It is allowable to use this raw material in a preparatorily molten state. It may be added, when necessary, in a solid state to the feed system. When the molten state is selected, the method which comprises installing a melting column for melting the solid raw material and keeping the molten raw material and feeding the molten raw material in an amount required from the melting column or the method which comprises melting the solid raw material in an amount conforming to the rate of feeding and feeding the molten raw material may be adopted, whichever better suits the occasion.

The method for production according to this invention does not need to be limited to the mode of embodiment described above. Naturally, it can be carried out by suitably combining the other modes of embodiment described above.

The chain trimer of orthophthalonitrile which is by-produced at the step of production of tetrachloroorthophthalonitrile by the method of this invention described above is a novel compound which is useful for such organic electronic materials as organic conductors, organic semiconductors, electrochromics, and electroluminescence. This chain trimer is represented by the general formula (2) as mentioned above. At the step of producing tetrachloroorthophthalonitrile by the method of this invention, for example, a condensing column is installed in the lower part of the evaporator when the molten orthophthalonitrile is fed continuously to the upper part of the evaporator kept in a temperature range of 260°–280° C. and nitrogen gas is likewise fed to the lower part of the evaporator and the mixture of the orthophthalonitrile with nitrogen is vaporized at a temperature of 260° C. Then, the self-condensate of orthophthalonitrile in a liquid state containing a chain trimer of orthophthalonitrile is condensed in the condensing column. This condensate is extracted, cooled to room temperature, then combined with acetone, and filtered to separate the substance insoluble in acetone. Otherwise, the orthophthalonitrile which remains in the evaporator after the reaction as described specifically afterward (Example 1) is likewise combined with acetone and filtered to separate the substance insoluble in acetone. Then, the insoluble substance is fractionally distilled to effect isolation of the chain trimer of orthophthalonitrile as a novel compound.

The raw material which can be used in this invention for the aromatic compound solid at room temperature has no particular limit to impose. All the aromatic compounds that are solid at room temperature and liable to yield to self-condensation are usable. As concrete examples of the aromatic compound which answers this description, phthalonitrile compounds such asorthophthalonitrile, isophthalonitrile, terephthalonitrile, monochloroorthophthalonitrile, dichloroorthophthalonitrile, and trichloroorthophthalonitrile; benzonitrile compounds such as dichlorobenzonitrile, trichlorobenzonitrile, and tetrachloro-benzonitrile; and pyridine compounds such as dicyanopyridine, dichlorocyanopyridine, and trichlorocyanopyridine may be cited. Among other aromatic compounds cited above, orthophthalonitrile and isophthalonitrile which can constitute themselves the raw materials for aromatic halongenides which are useful as intermediate raw materials for medicines, agricultural chemicals, functional pigments, and functional polymers prove particularly advantageous.

The halogen gas which can be used in this invention has no particular limit to impose. Chlorine gas and bromine gas can be cited as concrete examples of the halogen gas. Among other halogen gases which are conceivable, chlorine gas which can constitute itself the raw material for aromatic halogenates useful as intermediate raw materials for medicines, agricultural chemicals, functional pigments, and functional polymers proves particularly advantageous.

The halogenated aromatic compound which is produced by vapor phase catalytic reaction can be manufactured by suitably selecting the aromatic compound and the halogen gas a raw materials, depending on the purpose of use and the type of application to be contemplated. As concrete examples of the ideal aromatic compound, tetrachloroorthophthalonitrile and tetrachloroisophthalonitrile which are useful as intermediate raw materials for medicines, agricultural chemicals, functional pigments, and functional polymers may be cited.

The method of this invention is effectively utilized in the manufacture of tetrachloroorthophthalonitrile particularly by using orthophthalonitrile as a raw material and subjecting this raw material to a vapor phase chlorination in the presence of a catalyst.

The present invention is also to a method for producing a nuclear halogenated (chlorinated) aromatic compound by causing a gas containing an aromatic compound possessing cyano groups to react in the gaseous phase with a halogen gas such as, for example, chlorine gas.

The catalyst of a long service life which can be used in this invention is a catalyst of activated carbon. The activated carbon to be used for the catalyst herein has an average pore diameter of not less than 12.2 Å, preferably in the range of 12.2–20 Å, as determined by the nitrogen adsorption method and a cumulative pore volume of not less than 0.45 g/cc, preferably in the range of 0.47–0.7 g/cc, in the range of diameters of 5–100 Å as determined by the steam adsorption method. The activated carbon catalyst is adopted because activated carbon manifests the highest activity and selectively. If the activated carbon used for the catalyst has an average pore diameter of less than 12.2 Å as determined by the nitrogen adsorption method, the catalyst will undergo deterioration and suffer a decrease in service life because the by-produced compound such as triazine compound adheres to the interiors of the pores and ultimately clogs the pores. Conversely, if the average pore radius exceeds 12.2 Å, the pores will not be easily clogged. This phenomenon gains in conspicuousness in proportion as the average pore diameters increases.

The compounds, therefore, severally have their own optimum average pore radius which will be specifically descried afterward. If the average pore diameter exceeds a certain level, the effect of rendering the phenomenon of clogging difficult will be saturated. The average pore diameter in the saturated state varies from one compound to another. If the average pore radius diameter 20 Å, an unduly high level, the amount of activated carbon required for the reaction of chlorination will have to be increased because the excess will result in decreasing the specific surface area and the active point of chlorination. If the average pore radius is unduly large, the disadvantage of embrittling the particulate structure will ensue.

If the activated carbon has a cumulative pore volume of less than 0.45 cc/g, in the range of radiuses of 5–100 Å, as determined by the steam adsorption method, the by-product will cumulatively adhere to the interiors of pores, covers the active points of chlorination on the surface of the activated carbon (including the inner surfaces of pores), and ultimately result in deteriorating the activity and curtailing the service life of catalyst. The cumulative pore volume of the activated carbon determined in the range of pore radiuses of 5–100 Å by the steam adsorption method is preferred to be as large as possible, though variable with the kind of activated carbon. In the case of the activated carbon of coconut shell, for example, the pore volume is preferably designed within the range of not exceeding 0.7 g/cc because any excess of 0.7 g/cc results in degrading the strength of activated carbon particles and embrittling the particulate structure of activated carbon.

The activated carbon to be used in this invention properly has a specific surface area of not less than 900 m$^2$/g, preferably in the range of 900–1800 m$^2$/g, as determined by the B.E.T. method (Brunauer-Emmett-Teller method). If the specific surface area is less than 900 m$^2$/g, the points of activity of chlorination on the surface of activated carbon (including the inner surfaces of pores) will be decreased and the conditions for satisfying the average pore radius and the cumulative pore volume mentioned above will not be easily attained. These factors form problems which confront the design of particles. In contrast, when the active carbon to be used as a specific surface area exceeding 900 m$^2$/g, the reaction of chlorination can be carried out at a low reaction temperature and the decomposition of the nitrile group by chlorination which tends to occur to a high temperature, therefore, can be prevented and the formation of by-products (condensates) which tend to occur at a high reaction temperature can be repressed, with the result that the deposition of the by-products on the surface of catalyst will be diminished and the service life of catalyst will be elongated.

The activated carbon which satisfies the aforementioned requirements concerning the average pore radius, cumulative pore volume, and specific surface area can be obtained by using coconut shell carbon as a raw material and properly adjusting the conditions for activating the coconut carbon with steam.

Though the activated carbon has no particular limit to impose concerning the size, it is preferred to be a finely divided powder in order to satisfy the requirements mentioned above and acquire outstanding mechanical strength. Properly, it is molded or pulverized in the form of particles having diameters in the range of 3.5–10 meshes, preferably 4–6.5 meshes.

The activated carbon, when necessary, may carry thereon one member or a mixture of two or more members selected from the group consisting of chlorides of alkali metals, alkaline earth metals, and transition metals. As typical examples of the metal chlorides mentioned above, lithium chloride, sodium chloride, potassium chloride, rubidium chloride, cesium chloride, beryllium chloride, magnesium chloride, calcium chloride, strontium chloride, barium chloride, aluminum chloride, iron chloride, manganese chloride, cobalt chloride, and nickel chloride may be cited. These metal chlorides are not always required to be added in the form of a chloride from the beginning. They may be added in the form of such inorganic acid salts as hydroxides, carbonates, hydrogen carbonates, nitrates, and phosphates, in the form of such organic acid salts as acetates, fumarates, and benzoates, or in the form of oxides. Otherwise, metal powders of calcium, magnesium, and manganese maybe directly added. They are chlorinated by a chlorinating treatment.

As typical examples of the aromatic compound possessing cyano groups which is usable as the raw material in the present invention, benzonitrile, phthalonitrile, isophthalonitrile, terephthalonitrile, 3-cyanopyridine, 2-cyanopyridine, 2,6-dicyanopyridine 3,5-dicyanopyridine, and 1,2,4,5-tetracyano-benzene may be cited. The compounds which are represented by the following structural formula (3)

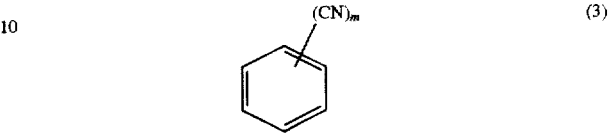

wherein m is an integer satisfying the expression 1≦m≦2) are preferably used. The nuclear chlorinated aromatic compound possessing cyano groups which is the product aimed at herein is only required to be obtained by suitably selecting a raw material from the group mentioned above, depending on the type of use contemplated, and chlorinating this raw material by using the method of this invention. The products which correspond to the concrete examples of raw material enumerated above are pentachlorobenzonitrile, tetrachlorophthalonitrile, tetrachloroisophthalonitrile, tetrachloroterephthalonitrile, 3-cyanotetrachloropyridine, 2-cyanotetrachloropyridine, 2,6-dicyanotrichloropyridine, 3,5-dicyanotrichloropyridine, and 1,2,4,5-tetracyanodichlorobenzene. The compounds represented by the following structural formula (4)

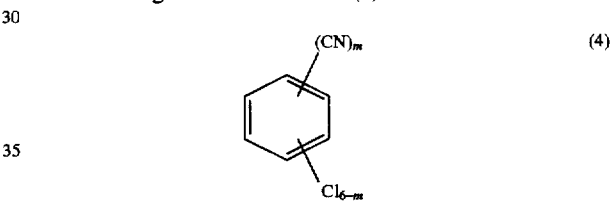

wherein m has the same numerical values as the symbol m in the structural formula (3) shown above, which are obtained by the chlorination of the raw materials of the structural formula (3) mentioned above according to the method of this invention are used preferably. In the benzonitriles, i.e. the compounds of the aforementioned structural formula having m=1, the activated carbon preferably has an average pore diameter in the range of 12.2–13.5 Å, as determined by the nitrogen adsorption method. In the phthalonitriles, i.e. the compounds of the aforementioned structural formula having m=2, the average pore radius of the activated carbon preferably is in the range of 12.5–15.0 Å.

For the sake of performing the reaction of vapor phase catalytic chlorination, the aforementioned raw material, i.e. the aromatic compound possessing cyano groups, is supplied in a gaseous form. The carrier gas which can contain the raw material in this case is only required to be insert to the raw material and to chlorine. Nitrogen gas, for example, is advantageously used because the carrier gas is preferred to be as inexpensive and readily available as permissible.

The method for the production of the nuclear chlorinated aromatic compound of this invention by the use of the activated carbon and the aromatic compound possessing cyano groups mentioned above may be any of the known methods which are used for vapor-phase catalytic chlorination. It can be carried out in accordance with the flow sheet for the production of a nuclear halogenated aromatic compound as illustrated in FIG. 3, for example. As shown in FIG. 4, the nitrogen gas containing an aromatic compound possessing cyano groups (benzonitrile, for example) as a raw material and chlorine gas are fed from a raw material feeding part (not shown) into a shell-and-tube reaction vessel 101 packed with an activated carbon catalyst contemplated by this invention as described above via a conduit 102 and left reacting in the gas phase. The nuclear chlorinated aromatic compound possessing cyano groups which is consequently produced is collected in a collector 104 via a conduit 103. The unaltered chlorine gas is forwarded via a conduit 105 into a waste gas disposing vessel 106 to be disposed of therein. Naturally, this invention does not need to be limited to the method of vapor-phase catalytic chlorination mentioned above.

Since the use of the activated carbon catalyst contemplated by this invention allows the reaction temperature to be lowered and the reaction velocity to be increased (and, consequently, the service life of the activated carbon catalyst to be elongated) as compared with the conventional method, the reaction of gas-phase catalytic chlorination in the reaction vessel 101 can be carried out under advantageous conditions. The individual conditions to be set can be suitably selected by any person of ordinary skill in the art, depending on the kind of a raw material, the amount of raw material to be treated, the scale of production facilities, and the kind of activated carbon catalyst. For the sake of obtaining pentachlorobenzonitrile (PCBN) as a product containing no low chloride where benzonitrile (BN) is selected as the raw material, for example, the reaction is advantageously performed at a reaction temperature exceeding 240° C., preferably falling in the range of 270°–350° C., a molar ratio of $Cl_2$/BN exceeding 6, preferably falling in the range of 7–12.5, a space velocity (S.V.) Falling in the range of 100–1500 $hr^{-1}$, preferably in the range of 200–1000 $hr^{-1}$, and a BN concentration falling in the range of 1.5–7.0 vol %, preferably in the range of 2.5–5.0 vol %. This reaction produces such highly satisfactory results as a BN conversion exceeding 98%, a yield (based on BN) exceeding 95 mol %, and a PCBN purity exceeding 95%. To obtain tetrachloroorthoorthophthalonitrile (TCPN) in a high yield where orthophthalonitrile (PN) is used as a raw material, the reaction is advantageously performed at a reaction temperature exceeding 220° C., preferably falling in the range of 250°–350° C., a molar ratio of $Cl_2$PN exceeding 5, preferably falling in the range of 6–10, a spatial velocity (S.V.) falling in the range of 100–1500 $hr^{-1}$, preferably in the range of 200–1000 $hr^{-1}$, and a PN concentration falling in the range of 0.5–5.0 vol %, preferably in the range of 2.0–3.0 vol %. This reaction produces such highly satisfactory results as a PN conversion exceeding 98%, a yield (based on PN) exceeding 95 mol %, and a PCBN purity exceeding 95%.

Though the reaction in the reaction vessel 101 is generally carried out under normal pressure, it may be performed under a decreased pressure or an increased pressure. It can be carried out in a fixed bed or in a fluidized bed. It can be performed either continuously or batchwise, whichever better suits the occasion.

Now, the method of this invention will be described more specifically below with reference to working examples.

EXAMPLE 1

From a metering feeder (produced by Kuma Engineering K.K. and marketed under trademark designation of "Acurater") as raw material feeing means, orthophthalonitrile powder was fed continuously to a kneader (produced by Kurimoto Tekkosho K.K. and marketed under product code of "S-4KRC") as transporting-melting means provided in the lower part thereof with a gear pump (produced by Chuorika K.K. and marketed under product code of "12-GR11"). It was transported through the interior of the kneader and meanwhile molten at 160° C.

Then, the molten orthophthalonitrile was continuously fed by the gear pump as liquid feeding means to an evaporator through the upper part thereof at a rate of 1.68 kg/hour. Nitrogen gas was continuously fed at a rate of 10.5 kg/hour to the evaporator through the lower part thereof and the mixture of orthophthalonitrile with nitrogen was vaporized in the evaporator at a temperature in the range of 210°–260° C. The residence time of the orthophthalonitrile in the molten state was seven minutes. The molten orthophthalonitrile was found to have a water content of 145 ppm. A self-condensate of phthalonitrile in the vapor was 0.20 mol % toorthophthalonitrile.

Chlorine gas was continuously fed at a rate of 6.02 kg/hour into the mixture of the orthophthalonitrile vapor with nitrogen gas and they were mixed in a mixer. The molar ratio of chlorine to orthophthalonitrile was set at 6.47.

The mixture of these gases was introduced into a reaction column packed with 37.8 liters of activated carbon (produced by Takeda Chemical Industries, Ltd. and marketed under trademark designation of "Shirasagi C2X4") and left reaction continuously at a reaction temperature of 280°–330° C. for 40 hours. Then, the product of chlorination was cooled to produce a crystalline powder. As a result, tetrachloroorthophthalonitrile, 99.4% in purity, was obtained in a yield of 96.7 mol % (based on the orthophthalonitrile fed as raw material).

The production line could be smoothly operated because it incurred no trouble due to clogging. The smooth operation of the line could be endorsed by the fact that the total amount of self-condensates of orthophthalonitrile formed in the transferring device, evaporator, and gas mixer was found by analysis to be only 0.20 mol % on the average based on the amount of the ortho-phthalonitrile fed as the raw material.

EXAMPLE 2

A kneader (produced by Kurimoto Tekkosho K.K. and marketed under product code of "S-4KRC") was installed at a position about 3 m higher than an evaporator so as to produce at the inlet to the evaporator a head pressure exceeding the inner pressure generated in the reaction system during the course of the reaction of chlorination and a check valve having a cracking pressure of 1 psi (produced by Nupro K.K. and marketed under product code of "SS-CHF4RT") was attached to the inlet part of the evaporator. Then, from a metering feeder (produced by Kuma Engineering K.K. and marketed under trademark designation of "Acurater"), orthophthalonitrile powder was fed continuously to a KRC kneader. It was transported through the interior of the kneader and meanwhile molten at 150° C.

Then, the molten orthophthalonitrile was continuously fed at a rate of 1.68 kg/hour to the upper part of the evaporator. The residence time of the orthophthalonitrile in the molten state before reaching the evaporator was about 1.5 minutes. The water content in the molten orthophthalonitrile was found by analysis to be 200 ppm. The self-condensate of phthalonitrile in the vapor was 0.20 mol % to orthophthalonitrile. Nitrogen gas was continuously fed at a rate of 10.5 kg/hour to the evaporator through the lower part thereof and the mixture of orthophthalonitrile with nitrogen was meanwhile vaporized at a temperature of 210°–260° C.

In a mixer, the mixture of the orthophthalonitrile vapor with nitrogen gas and nitrogen gas continuously fed at a rate of 6.02 kg/hour therein were mixed. The molar ratio of chloride to orthophthalonitrile was set at 6.47.

The mixture of these gases was introduced into a reaction column packed with 37.8 liters of activated carbon and left reacting continuously therein at a reaction temperature of 280°–330° C. for 40 hours. Then, the product of chlorination was cooled and collected in the form of a powder of crystals in a collector. As a result, tetrachloroorthophthalonitrile, 99.6% in purity, was obtained in a yield of 96.2 mol % (based on the amount of orthophthalonitrile fed as a raw material).

The total amount of self-condensates of orthophthalonitrile formed in the transferring device, evaporator, and gas mixer was found by analysis to be 0.12 mol % on the average based on the amount of therothophthalonitrile fed as the raw material.

EXAMPLES 3–5

Orthophthalonitrile was transported, molten, and subjected to a reaction by following the procedure of Example 1 while changing the gear pump as liquid feeding means to the pumps shown in Table 1 and changing the residence time of orthophthalonitrile in the molten state to the lengths of time shown in Table 1. As a result, the test results [(a) the water content in the molten orthophthalonitrile, (b) the yield of tetrachloroorthophthalonitrile (based on the amount of orthophthalonitrile fed), (c) the purity of tetrachloroorthophthalonitrile, and (d) the total amount of self-condensates of orthophthalonitrile in transporting device, evaporator, and mixer] shown in Table 1 were obtained. The self-condensate of phthalonitrile in the vapor was 0.20 mol % toorthophthalonitrile.

TABLE 1

| Example | Pump | Residence time (min.) | Water content (ppm) | Yield (mol %) | Purity (%) | Amount of formed self-condensate (mol %) |
|---|---|---|---|---|---|---|
| Example 3 | K. K. Iwaki Hicera Pump | 8 | 200 | 97.2 | 99.4 | 0.20 |
| Example 4 | K. K. Sakura Seisakusho CDQ J103-1 | 30 | 160 | 95.4 | 99.2 | 0.25 |
| Example 5 | Tathill D 7006FC-X | 10 | 120 | 97.6 | 99.5 | 0.07 |

EXAMPLE 6

From a metering feeder (produced by Kuma Engineering K.K. and marketed under trademark designation of "Acurater") as raw material feeding means, orthophthalonitrile powder was fed continuously to a kneader (produced by Kurimoto Tekkosho K.K. and marketed under product code of "S-4KRC") as transporting=melting means provided in the lower part thereof with a small pot, about 1 liter in inner volume, for storing molten phthalonitrile as the raw material and a diaphragm pump (produced by Sakara Seisakusho K.K. and marketed under product code of "CDQJIO3-I"). It was transported through the interior of the kneader and meanwhile molten at 160° C.

Then, the molten orthophthalonitrile was provisionally stored in a small pot, about 1 liter in inner volume, and then fed continuously at a rate of 1.68 kg/hour to the upper part of the evaporator by means of the diaphragm pump as transporting means. A check valve having a cracking pressure of 1 psi (produced by Nupro K.K. and marketed under product code of "SS-CHF4RT") was attached to the upper part of the evaporator for the purpose of preventing backflow. Nitrogen gas was continuously fed from the lower part of the evaporator at a rate of 10.5 kg/hour and the mixture of orthophthalonitrile with nitrogen was meanwhile vaporized at a temperature of 210°–260° C. The residence time of the orthophthalonitrile in the molten state was about 30 minutes. The self-condensate of phthalonitrile in the vapor was 0.20 mol % to orthophthalonitrile. The water content in the molten orthophthalonitrile was found by analysis to be 1000 ppm. The mixture of the orthophthalonitrile vapor with nitrogen gas and chlorine gas continuously fed at a rate of 6.02 kg/hour thereto was mixed in a mixer. The molar ratio of chlorine to orthophthalonitrile was set at 6.47.

The mixture of these gases was introduced into a reaction column packed with 37.8 liters of activated carbon (produced by Kuraray Chemical K.K. and marketed under trademark designation of "Kuraray Coal 4GS") and left reacting continuously at a reaction temperature of 265°–275° C. for 84 hours. Then, the product of chlorination was cooled to produce a powder of crystals. As a result, tetrachloroorthophthalonitrile, 99.5% in purity, was obtained in a yield of 99.9 mol % (based on the amount of orthophthalonitrile fed).

The production line could be smoothly operated because it incurred no trouble due to clogging. The smooth operation of the line could be endorsed by the fact that the total amount of self-condensates of orthophthalonitrile formed in the transferring device, evaporator, and gas mixer was found by analysis to be only 0.4 mol % on the average based on the amount of the ortho-phthalonitrile fed as the raw material.

EXAMPLE 7

Orthophthalonitrile was transported, molten, and subjected to a reaction by following the procedure of Example 4 while having a check valve attached to the upper part of the evaporator for preventing backflow in the same manner as in Example 6, changing the water content in the orthophthalonitrile powder as the raw material to 800 ppm, and changing the residence time of orthophthalonitrile in the molten state to 50 minutes. The self-condensate of phthalonitrile in the vapor was 0.20 mol % to orthophthalonitrile. As a result, tetrachloroorthophthalonitrile, 99.2% in purity, was obtained in a yield of 95.3 mol % (based on the amount of orthophthalonitrile fed as a raw material). The total amount of self-condensates of orthophthalonitrile formed in the transferring device, evaporator, and gas mixer was found by analysis to be 1.6 mol % on the average based on the amount of the orthophthalonitrile fed as the raw material.

EXAMPLE 8

Molten orthophthalonitrile was continuously fed at a rate of 1.49 kg/hour to the upper part of an evaporator kept at a temperature in the range of 260°–280° C. and chlorine gas was continuously fed at a rate of 10.7 kg/hour to the lower part of the evaporator and the orthophthalonitrile was vaporized at a temperature of 260° C. The self-condensate of phthalonitrile in the vapor was 0.20 mol % to orthophthalonitrile. Simultaneously with the vaporization of orthophthalonitrile, the self-condensate of liquid orthophthalonitrile having a solid substance partly mixed therein was condensed in a condensing column installed in the lower part of the evaporator and was extracted from the lower part from time to time. The self-condensates of orthophthalonitrile were a dark blue substance (amount formed: 0.023 kg/hour), which was found by analysis to consist of about 75% of a trimer (melting point 125° C.) having orthophthalonitrile moieties linked in the form of a chain and about 20% of phthalocyanine compounds. A mixture of orthophthalonitrile vapor with nitrogen gas and chlorine gas fed continuously at a rate of 4.94 kg/hour therein were mixed in a mixer. The molar ratio of chlorine to orthophthalonitrile was set at 6. The content of the self-condensates of orthophthalonitrile in the mixture of gases was found by analysis to be 1.9 mol % based on the amount of orthophthalonitrile.

The mixture of these gases was introduced into a reaction column packed with 40 liters of activated carbon (produced by Takeda Chemical industries, Ltd. and marketed under trademark designation of "Shirasagi-C2X4") and left reacting continuously at a reaction temperature of 290°–310° C. for 60 hours. Then, the product of chlorination was cooled to produce a crystalline powder. As a result, tetrachloroorthophthalonitrile, 99.0% in purity, was obtained in a yield of 90.6 mol % (based on the orthophthalonitrile fed as raw material).

Control 1

Orthophthalonitrile was processed by following the procedure of Example 8 while omitting the provision of a condensing column in the lower part of the evaporator and consequently omitting the separation of self-condensates of orthophthalonitrile. As a result, the pressure in the reaction system rose to the extent of preventing the operation of the reaction system from proceeding after 18 hours following the start of the reaction. The purity of the produced tetraorthophthalonitrile was 97.1%.

EXAMPLE 9

In a melting column, 0.2 m³ in inner volume, lined with glass, orthophthalonitrile in a powdery form was introduced from time to time and molten by being heated to 160° C. Then, the molten orthophthalonitrile was introduced by a pump into an evaporator. Prior to this introduction, the molten orthophthalonitrile was passed at a rate of 1.5 kg/hour through a strainer interposed between the melting column and the evaporator, more precisely between the melting column and the pump, and kept in a temperature range of 180°–200° C. to remove self-condensates of orthophthalonitrile formed in a solid state in the melting column. The self-condensates of orthophthalonitrile separated on the strainer were a bluish purple substance (formed at a rate of 0.012 kg/hour), which was found by analysis to consist substantially solely of phthalocyanine compounds.

The molten orthophthalonitrile which passed through the strainer was continuously fed to the upper part of the evaporator kept in a temperature range of 260°–280° C. and nitrogen gas was likewise fed at a rate of 10.7 kg/hour to the lower part of the evaporator and the orthophthalonitrile was vaporized at a temperature of 260° C. The self-condensate of phthalonitrile in the vapor was 1.0 mol % to orthophthalonitrile. Simultaneously with the vaporization of orthophthalonitrile, the self-condensates of orthophthalonitrile in a liquid state were condensed in a condensing column disposed in the lower part of the evaporator and extracted from the lower part from time to time. The self-condensates of orthophthalonitrile separated from the lower layer part of the evaporator were a dark blue substance (formed at a rate of 0.018 kg/hour), which was found by analysis to consist substantially solely of a trimer, 125° C. in melting point, having moieties of orthophthalonitrile linked in the form of a chain. The mixture of the orthophthalonitrile vapor with nitrogen gas and chlorine gas fed continuously thereto at a rate of 4.94 kg/hour were mixed in a mixer. The molar ratio of chlorine to orthophthalonitrile was et at 6. The content of the self-condensates of orthophthalonitrile in the mixture of gases was found by analysis to be 1.5 mol % based on the amount of orthophthalonitrile.

The mixture of these gases was introduced into a reaction column packed with 40 liters of activated carbon (produced by Takeda Chemical industries, Ltd. and marketed under trademark designation of "Shirasagi-C2X4") and left reacting continuously at a reaction temperature of 290°–310° C. for 66 hours. Then, the product of chlorination was cooled to produce a crystalline powder. As a result, tetrachloroorthophthalonitrile, 99.1% in purity, was obtained in a yield of 90.2 mol % (based on the orthophthalonitrile fed as raw material.

Control 2

Orthophthalonitrile was processed by following the procedure of Example 9 while omitting the provision of a strainer after the melting column. After 8 hours following the start of the reaction, the pump for feeding the molten orthophthalonitrile to the evaporator ceased to operate and the operation of the apparatus could not be continued any longer.

EXAMPLE 10

In a melting column, 0.2 m³ in inner volume, lined with glass, orthophthalonitrile in a powdery form was introduced from time to time and molten by being heated to 160° C. Then, the molten orthophthalonitrile was introduced by a pump into an evaporator. Prior to this introduction, the molten orthophthalonitrile was passed at a rate of 1.5 kg/hour through a strainer interposed between the melting column and the evaporator, more precisely between the melting column and the pump, and kept in a temperature range of 180°–200° C. to remove self-condensates of orthophthalonitrile formed in a solid state in the melting column. The self-condensates of orthophthalonitrile separated on the strainer were a bluish purple substance (formed at a rate of 0.012 kg/hour), which was found by analysis to consist substantially solely of phthalocyanine compounds.

The molten orthophthalonitrile which passed through the strainer was continuously fed to the upper part of the evaporator kept in a temperature range of 260°–280° C. and nitrogen gas was likewise fed at a rate of 10.7 kg/hour to the lower part of the evaporator and the orthophthalonitrile was vaporized at a temperature of 260° C. Simultaneously with the vaporization of orthophthalonitrile, the self-condensates of orthophthalonitrile in a liquid state were condensed in a condensing column disposed in the lower part of the evaporator and extracted from the lower part from time to time. The self-condensates of orthophthalonitrile separated from the lower part of the evaporator were a dark blue substance (formed at a rate of 0.018 kg/hour), which was found by analysis to consist substantially solely of a trimer, 125° C. in melting point, having moieties of orthophthalonitrile linked in the form of a chain.

Then, the mixture of the orthophthalonitrile vapor with nitrogen gas and chlorine gas continuously fed at a rate of 4.94 kg/hour thereto were mixed in a mixer. The gas mixture was introduced into a trap made of a ceramic perforated plate and glass wool, interposed between the evaporator and the reaction column, more precisely between the mixer and the reaction column, for the purpose of collecting the self-condensates of orthophthalonitrile entrained in the orthophthalonitrile-containing gas in the composition of gas mixture, and kept at 200° C. to separate from the gas mixture the self-condensates of orthophthalonitrile entrained in the orthophthalonitrile-containing gas. The separated self-condensates were extracted from the trap from time to time. The content of the self-condensates of orthophthalonitrile in the gas mixture which passed through the trap was found by analysis to be 0.3 mol % based on the amount of orthophthalonitrile. The self-condensates of orthophthalonitrile extracted from the trap were a yellowish brown substance (formed at a rate of 0.025 kg/hour), which was found by analysis to consist substantially solely of 2,4,6-tri(o-cyanophenyl)-1,3,5-triazine, 290° C. in melting point and 310° C. in boiling point, a timer having moieties of orthophthalonitrile connected in the form of a ring.

The mixture of these gases was introduced into a reaction column packed with 40 liters of activated carbon (produced by Takeda Chemical Industries, Ltd. and marketed under trademark designation of "Shirasagi-C2X4") and left reacting continuously at a reaction temperature of 290°–310° C. for 78 hours. Then, the product of chlorination was cooled to produce a crystalline powder. As a result, tetrachloroorthophthalonitrile, 99.6% in purity, was obtained in a yield of 91.2 mol % (based on the orthophthalonitrile fed as raw material).

EXAMPLE 11

In a bubbling type evaporator, 5 liters in inner volume, made of glass, 4.0 kg of orthophthalonitrile was placed and molten by being heated to 180° C. To the evaporator, nitrogen gas was continuously supplied at a rate of 474.7 g/hour, with orthophthalonitrile entrained thereby at a rate of 70 g/hour. The mixture of the orthophthalonitrile vapor with nitrogen gas and chlorine gas continuously fed thereto at a rate of 310.4 g/hour were mixed. The molar ratio of orthophthalonitrile to chlorine was set at 8. The self-condensate of phthalonitrile in the vapor was 1.2 mol % to orthophthalonitrile.

The mixture of these gases was introduced into a U-shaped reaction column, 27.8 cm in inside diameter, made of nickel and packed with 1400 ml of activated carbon (produced by Takeda Chemical industries, Ltd. and marketed under trademark designation of "Shirasagi-C2X4") and left reacting continuously at a reaction temperature of 330° C. for 25 hours. Then, the product of chlorination was cooled to produce a crystalline powder. As a result, 3.6 kg of tetrachloroorthophthalonitrile, 99.3% in purity, was obtained.

The orthophthalonitrile fed to the reaction system herein was found to have a water content of 110 ppm and was confirmed by analysis with fluorescent X ray to contain iron, nickel, zinc, manganese, aluminum, copper, cobalt, and chromium in a total amount of not more than 20 ppm.

Of the amount, 2.1 kg, of the orthophthalonitrile remaining in the evaporator after the reaction;

(a) A sample was separated into an acetone-soluble fraction and an acetone-insoluble fraction and these fractions were evaporated to dryness to expel acetone and the respective solid residues were weighed.

(b) Part of the acetone-soluble fraction was collected and analyzed by gas chromatography to find the orthophthalonitrile content.

(c) Since the chain trimer of orthophthalonitrile contained in the acetone-soluble fraction has an absorption in the visible zone (670–680 nm), a sample of the fraction was tested for molar extinction coefficient and assayed with a spectrophotometer (UV-IR).

(d) The acetone-insoluble fraction was assayed with a spectrophotometer (UV-IR) in the same manner as above to find the contents of phthalocyanine compound and triazine compound.

the results of (a)–(d) above indicate that the residual orthophthalonitrile, 2.1 kg in amount, was composed of 1940 g of the unaltered orthophthalonitrile, 40 g of the chain trimer of orthophthalonitrile (melting point 125° C., M$^+$: 385), 25 g of phthalocyanine compounds, and 40 g of the cyclic trimer of orthophthalonitrile (melting point 290° C., boiling point 310° C., M$^+$: 384). The amount of the self-condensates of orthophthalonitrile was confirmed to be 2.6% of 4 kg of orthophthalonitrile fed to the reaction.

EXAMPLES 12–16 AND CONTROLS 3–6

Service life are conducted for testing of the catalysts under harsh reaction conditions to effect accelerated rating of the performance.

The reaction conditions of the accelerated test were set at S.V. of 1000 hr$^{-1}$, BN gas concentration of 5%, and hot bath temperatures of 350° C. where the raw materials in Examples 12 and 13 and Controls 3 and 4 were benzonitrile. They were set at S.V. 1000$^{-1}$, phthalonitrile gas concentration of 3%, and hot bath temperature of 350° C. where the raw materials in Examples 14–15 and Controls 5 and 6 were phthalonitrile.

EXAMPLE 12

As an activated carbon catalyst, 60 cc of activated carbon A |formed of coconut shell activated carbon having an average pore diameter of 12.6 A determined by the nitrogen adsorption method (hereinafter referred to briefly as "average pore diameter"), a cumulative pore volume of 0.48 g/cc in the region of activated carbon possessing pore diameters of 5–100 Å determined by the steam adsorption method (hereinafter referred to briefly as "cumulative pore volume"), and a specific surface area of 902 m$^2$/g determined by the B.E.T. method (hereinafter referred to briefly as "specific surface area")] was packed in a reaction column of nickel, 26 mm in inside diameter.

This reaction column was immersed in a hot bath kept at a temperature of 350° C. The mixture of chlorine gas fed at a rate of 160 ml of per minute with nitrogen gas fed at a rate of 480 ml per minute was passed through the reaction column for one hour to activate the catalyst with chlorine. Subsequently, chlorine gas fed at a rate of 545 ml per minute was passed in BN and the gas produced by the resultant gasification and caused to entrain BN at a rate of 55 ml per minute was mixed with chlorine gas fed at a rate of 490 ml per minute. The resultant mixture was passed through the reaction column to induce a reaction of the reactants in the mixture. In this case, the S.V. of reaction was 1000 hr$^{-1}$, the BN gas concentration was 5%, and the molar ratio of chlorine to BN was 9 (1.8 times the theoretically required level). During the reaction, the temperature of the hot bath was kept at 350° C.

The solid substance formed during the reaction was collected in a crystallizing device. At fixed intervals, the product thus collected was weighed and analyzed by gas chromatography to determine the purity and yield of PCBN.

The period in which such fine results as more than 98% of BN conversion, more than 92 mol % of yield (based on BN), and more than 93% of PCBN purity were obtained was defined as the service life of the catalyst. The results of the test for service life of catalyst are shown in Table 1.

EXAMPLE 13 AND CONTROLS 3 AND 4

A test for service life of catalyst was performed by following the procedure of Example 12.

In Example 13 and Controls 3 and 4, a reaction of vaporphase catalytic chlorination was carried out by following the procedure of Example 12 while using activated carbon B (formed of coconut shell activated carbon having an average pore diameter of 12.9 Å, a cumulative pore volume of 0.52 g/cc, and a specific surface area of 1020 m$^2$/g) in Example 13, activated carbon C (formed of coconut shell activated carbon having an average pore radius of 12.0 Å, a cumulative pore volume of 0.43 g/cc, and a specific surface area of 889 m$^2$/g) in Control 8, and activated carbon D (formed of coal activated carbon having an average pore radius of 11.2 Å, a cumulative pore volume of 0.57 g/cc, and a specific surface area of 1440 m$^2$/g) in Control 9 respectively in the place of the activated carbon A to determine the service lives of the activated carbons. The results are shown in Table 2.

TABLE 2

| | Catalyst | Specific surface area (m$^2$/g) | Average pore diameter (Å) | Accumulated pore volume (cc/g) | Life of catalyst (hr) |
|---|---|---|---|---|---|
| Example 12 | Activated Carbon A | 902 | 12.5 | 0.48 | 310 |
| Example 13 | Activated Carbon B | 1,020 | 12.9 | 0.52 | 290 |
| Control 3 | Activated Carbon C | 889 | 12.0 | 0.43 | 220 |
| Control 4 | Activated Carbon D | 1,440 | 11.2 | 0.57 | 240 |

EXAMPLE 14

This example used the same activated carbon catalyst as in Example 12 and the same apparatus as in Example 12, with the activated carbon packed in the reaction column of the apparatus.

The reaction column was immersed in a hot bath kept at a temperature of 350° C. The mixture of chlorine gas fed at a rate of 160 ml per minute with nitrogen gas fed at a rate of 480 ml per minute was passed through the reaction column for one hour to activate the catalyst with chlorine. Subsequently, chlorine gas fed at a rate of 830 ml per minute was passed in BN and the gas produced by the resultant gasification and caused to entrain BN at a rate of 33 ml per minute was mixed with chlorine gas fed at a rate of 229 ml per minute. The resultant mixture was passed through the reaction column to induce a reaction of the reactants in the mixture. In this case, the S.V. of reaction was 1000 hr$^{-1}$, the PN gas concentration was 3%, and the molar ratio of chlorine to PN was 7 (1.75 times the theoretically required level). During the reaction, the temperature of the hot bath was kept at 350° C.

The solid substance formed during the reaction was collected in a crystallizing device. At fixed intervals, the product thus collected was weighed and analyzed by gas chromatography to determine the purity and yield of TCPN.

The period in which such fine results as more than 98% of BN conversion, more than 92 mol % of yield (based on BN), and more than 93% of PCBN purity were obtained was defined as the service life of the catalyst. The results of the test for service life of catalyst are shown in Table 3.

EXAMPLES 15 and 16 and Controls 5 and 6

A test for service life of catalyst was performed by following the procedure of Example 14.

In Examples 15 and 16 and Controls 5 and 6, a reaction of vapor phase catalytic chlorination was carried out by following the procedure of Example 14 while using activated carbon B (formed of coconut shell activated carbon having an average pore radius of 12.9 Å, a cumulative pore volume of 0.52 g/cc, and a specific surface area of 1020 m$^2$/g) in Example 15, activated carbon C (formed of coconut shell activated carbon having an average pore radius of 23.3 Å, a cumulative pore volume of 0.56 g/cc, and a specific surface area of 995 m$^2$/g) in Example 16, activated carbon C (formed of coconut shell activated carbon having an average pore diameter of 12.0 Å, a cumulative pore volume of 0.43 g/cc, and a specific surface area of 889 m$^2$/g) in Control 5, and activated carbon D (formed of coal activated carbon having an average pore diameter of 11.2 Å, a cumulative pore volume of 0.57 g/cc, and a specific surface area of 1440 m$^2$/g) in Control 6 respectively in the place of the activated carbon A to determine the service lives of the activated carbons. The results are shown in Table 3.

TABLE 3

| | Catalyst | Specific surface area (m$^2$/g) | Average pore diameter (Å) | Accumulated pore volume (cc/g) | Life of catalyst (hr) |
|---|---|---|---|---|---|
| Example 14 | Activated Carbon A | 902 | 12.6 | 0.48 | 180 |
| Example 15 | Activated Carbon B | 1,020 | 12.9 | 0.52 | 270 |
| Example 16 | Activated Carbon C | 995 | 13.3 | 0.56 | 240 |
| Control 5 | Activated Carbon D | 889 | 12.0 | 0.43 | 100 |
| Control 6 | Activated Carbon E | 1,440 | 11.2 | 0.57 | 80 |

The entire disclosure of Japanese Patent Application Nos. 8-050260 filed on Mar. 7, 1996, 8-070627 filed on Mar. 28, 1996, 8-151320 filed on Jun. 12, 1996, 8-263180 filed on Oct. 3, 1996 and 9-037836 filed on Feb. 21, 1997 including specification, claims, drawings and summary are incorporated herein by reference in its entirely.

What is claimed is:

1. A method for producing a nuclear halogenated aromatic compound possessing cyano groups by using as a raw material an aromatic compound which possesses cyano groups and assumes a solid state at room temperature and subjecting said raw material to a procedure comprising a step of melting and transporting said compound by a means for transport-melting, a step of vaporizing said compound, a step of mixing the vapor of said compound with a halogen gas, and a step of causing the vapor of said compound to react with said halogen gas in a vapor phase in the presence of a catalyst sequentially in the order mentioned, which comprises maintaining a content of a self-condensate of said aromatic compound possessing cyano groups in a vapor of said aromatic compound which reacts with the halogen gas to a level of not more than 2.5 mol % based on said compound.

2. A method according to claim 1, wherein a residence time in the molten state of said aromatic compound possessing cyano groups at the step for melting and transporting said compound is not more than 120 minutes.

3. A method according to claim 1, wherein the water content of said aromatic compound is not more than 2000 ppm based on the amount of said aromatic compound possessing cyano groups at the step for melting and transporting said compound.

4. A method according to claim 1, wherein said raw material in a solid state is fed by raw material feed means to said transporting-melting means and said solid raw material is melted by said transporting-melting means at the step for melting and transporting said aromatic compound possessing cyano groups.

5. A method according to claim 4, wherein said transporting-melting means at the step for melting and transporting said aromatic compound possessing cyano groups is a feeding device provided with a constant feeding mechanism.

6. A method according to claim 1, wherein said transporting-melting means for melting said raw material being transported is operated by the use of a continuous mixing and transporting device provided with a heating mechanism at the step of melting and transporting said aromatic compound possessing cyano groups.

7. A method according to claim 1, wherein molten said raw material is fed to a subsequent vaporization step by further providing a liquid transfer means subsequently to said transporting-melting means at the step for melting and transporting said aromatic compound possessing cyano groups.

8. A method according to claim 7, wherein said liquid transfer means is a hot liquid transporting device provided with a constant feeding mechanism.

9. A method according to claim 1, wherein a condensing part is provided in an evaporator maintained at a temperature exceeding a dew point of said aromatic compound possessing cyano groups for evaporating said compound at a step for evaporating said compound, wherein said self-condensate of the aromatic compound possessing cyano groups is liquefied and then the liquefied self-condensate is removed from the condensing part on demand.

10. A method according to claim 1, wherein said aromatic compound possessing cyano groups and assuming a solid state at room temperature is orthophthalonitrile, said halogen gas used for said reaction is chlorine gas, and said nuclear halogenated aromatic compound produced by said reaction is tetrachloroorthophthalonitrile.

11. A method according to claim 10, wherein the self-condensate of said aromatic compound possessing cyano groups is a chain polymer substance of an orthophthalonitrile represented by the following general formula (1):

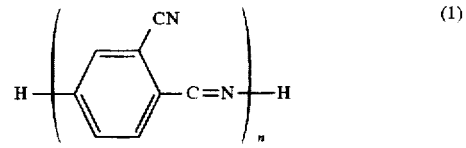

wherein n represents an integer in the range of 2–8.

12. A method according to claim 10, wherein the self-condensate of said aromatic compound possessing cyano groups is a phthalocyanine compound.

13. A method according to claim 10, wherein the self-condensate of said aromatic compound possessing cyano groups is 2,4,6-tri(o-cyanophenyl)-1,3,5-triazine.

14. A chain trimer compound represented by the formula (2):

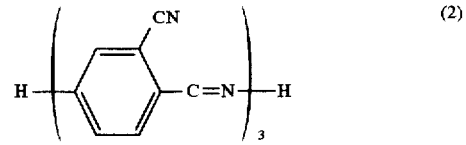

15. A method according to claim 1, wherein said catalyst is an activated carbon and said activated carbon being such that the average pore diameter of said activated carbon determined by the nitrogen adsorption method is not less than 12.2 Å and the cumulative pore volume of the portion of said activated carbon having pore diameters in the range of 5–100 Å determined by the steam adsorption method is not less than 0.45 g/cc.

16. A method according to claim 15, wherein the specific surface area of said activated carbon as determined by the B.E.T. method is not less than 900 $m^2/g$.

* * * * *

UNITED STATES PATENT AND TRADEMARK OFFICE
CERTIFICATE OF CORRECTION

PATENT NO. : 5,789,582  Page 1 of 2
DATED : August 4, 1998
INVENTOR(S) : Osama Kaida, et al.

It is certified that error appears in the above-identified patent and that said Letters Patent is hereby corrected as shown below:

On the tile page, Item [56], add the following references,

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 3 | 8 | 3 | 9 | 4 | 0 | 1 | 10/1/74 | Lavergne et al. | | | |
| | | 4 | 4 | 8 | 5 | 0 | 5 | 0 | 11/27/84 | Casale et al. | | | |
| | | | | | | | | | | | | | |

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | JP- | B- | 43- | 02 | 22 | 9 | 8 | 9/25/68 | Japan | | | | |
| | JP- | B- | 44- | 29 | 8 | 5 | 3 | 12/3/69 | Japan | | | | |
| | JP- | B- | 50- | 03 | 80 | 8 | 9 | 10/1/74 | Japan | | | | |
| | DE- | A- | 19 | 32 | 4 | 2 | 1 | 1/28/71 | Germany | | | | |
| | DE- | A- | 23 | 51 | 9 | 4 | 7 | 4/25/74 | Germany | | | | |
| | | | | | | | | | | | | | |

UNITED STATES PATENT AND TRADEMARK OFFICE
CERTIFICATE OF CORRECTION

PATENT NO. : 5,789,582
DATED : August 4, 1998
INVENTOR(S) : Osama Kaida, et al.

It is certified that error appears in the above-identified patent and that said Letters Patent is hereby corrected as shown below:

FOREIGN PATENT DOCUMENTS

| | | DOCUMENT NUMBER | | | | | PUBLICATION DATE | COUNTRY OR PATENT OFFICE | CLASS | SUBCLASS | TRANSLATION YES | NO |
|---|---|---|---|---|---|---|---|---|---|---|---|---|
| | | GB- A- | 12 | 44 | 3 | 8 | 7 | 9/2/71 | Great Britain | | | | |
| | | GB- A- | 13 | 04 | 7 | 3 | 4 | 1/31/73 | Great Britain | | | | |
| | | JP- A- | 59- | 02 | 16 | 5 | 8 | 2/3/84 | Japan | | | | |
| | | JP- B- | 63- | 06 | 50 | 6 | 5 | 12/14/88 | Japan | | | | |

OTHER DOCUMENTS

| | | |
|---|---|---|
| | European Search Report. 6/26/97 | |
| | Chemical Abstracts, Vol. 100, No. 25, Abstract No. 209427 corresponding to | |
| | JP-A-59-021658 (JP-B-63-065065) and US-A-4, 485, 050. 6/18/84 | |

Signed and Sealed this

Fourth Day of May, 1999

*Attest:*

Q. TODD DICKINSON

*Attesting Officer*   Acting Commissioner of Patents and Trademarks